United States Patent [19]

Idelson et al.

[11] 4,206,139
[45] Jun. 3, 1980

[54] SYNTHESIS OF BENZALDEHYDES

[75] Inventors: Elbert M. Idelson, West Newton; Charles E. Jandrue, Norwood, both of Mass.

[73] Assignee: Polaroid Corporation, Cambridge, Mass.

[21] Appl. No.: 946,110

[22] Filed: Sep. 27, 1978

Related U.S. Application Data

[63] Continuation-in-part of Ser. No. 856,220, Dec. 1, 1977, abandoned.

[51] Int. Cl.$^2$ ............... C07C 68/06; C07C 45/00; G03C 5/54
[52] U.S. Cl. ............... 260/463; 260/438.1; 260/438.5 R; 430/225; 568/426; 568/437; 568/442
[58] Field of Search ............... 260/463, 600 R

[56] References Cited

U.S. PATENT DOCUMENTS

| | | | |
|---|---|---|---|
| 3,544,545 | 12/1970 | Idelson | 260/600 |
| 3,563,739 | 2/1971 | Idelson | 96/29 |
| 3,597,200 | 8/1971 | Idelson | 96/29 |
| 3,629,336 | 12/1971 | Idelson | 260/600 |
| 3,705,184 | 12/1972 | Goulston et al. | 260/438.5 R |
| 3,752,836 | 8/1973 | Idelson | 260/438.5 R |
| 3,770,833 | 11/1973 | Bader et al. | 260/600 |

*Primary Examiner*—Donald G. Daus
*Assistant Examiner*—M. C. Eakin
*Attorney, Agent, or Firm*—Gaetano D. Maccarone

[57] ABSTRACT

Novel benzaldehydes of the formula:

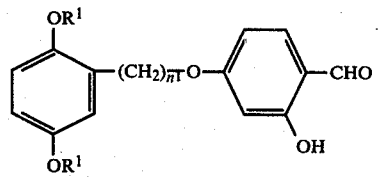

Where $n^1$ is the integer 1–8 and each $OR^1$ group is hydroxy or a protective group which can be converted or removed to provide the dihydroxyphenyl moiety.

The benzaldehydes are particularly useful as intermediates in the preparation of yellow azomethine dye developers.

8 Claims, 5 Drawing Figures

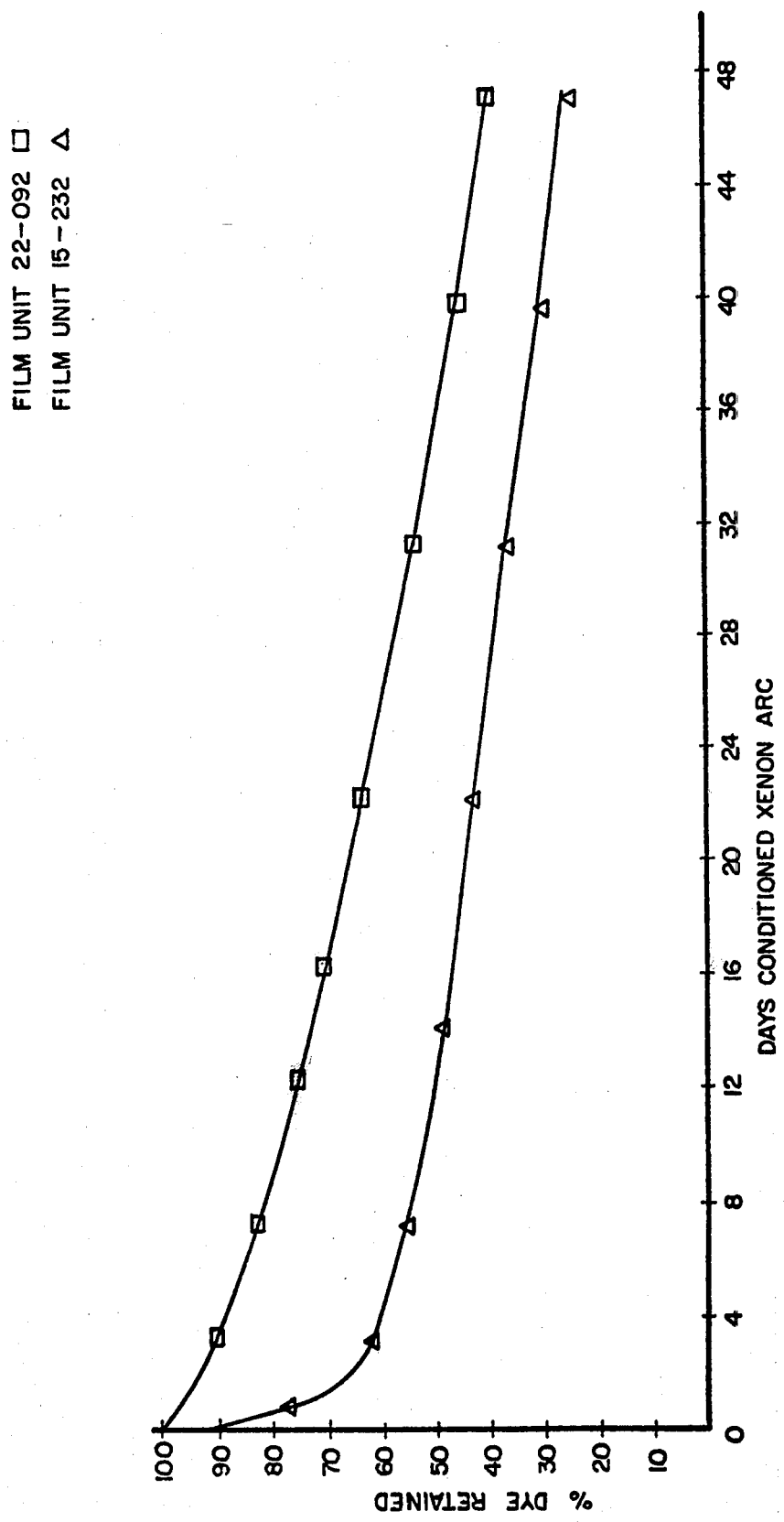

SYNTHESIS OF BENZALDEHYDES

CROSS REFERENCE TO RELATED CASES

This application is a continuation of prior copending application Ser. No. 856,220, filed Dec. 1, 1977 and now abandoned.

BACKGROUND OF THE INVENTION

1. The Field of the Invention

This invention relates to novel benzaldehydes having a silver halide developing capability and which are particularly useful as intermediates for the preparation of yellow azo methine dyes having particularly desirable performance characteristics in photographic products and processes.

2. Description of the Prior Art

Yellow dyes having a silver halide developing capability, e.g., a silver halide developing substituent are known to the art. Such dyes, commonly referred to as "dye developers", are disclosed in the following U.S. Pat. Nos.: 3,134,672; 3,134,764: 3,135,604; 3,135,734; 3,141,772; 3,183,090; 3,309,199; 3,424,742; 3,597,200; 3,705,184 and 3,752,836.

Of the above Patents, U.S. Pat. Nos. 3,597,200; 3,705,184 and 3,752,836 particularly relate to yellow dye developers having azomethine dyes chrome complexed to a substantially colorless ligand which provides the substituent having the silver halide developing capability. The yellow azomethine dyes of these Patents are of the following general formula:

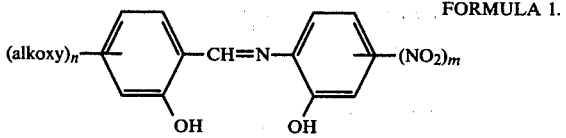

FORMULA 1.

where the alkoxy moiety contains 1–8 carbon atoms and n and m each are the integers 1 or 2.

As described in these Patents and particularly in U.S. Pat. No. 3,705,184, the yellow ortho, ortho' dihydroxy azomethine dyes of Formula 1 can be prepared by reacting an alkoxy-substituted o-hydroxybenzaldehyde with a nitro-substituted o-hydroxyaniline according to the following reaction scheme:

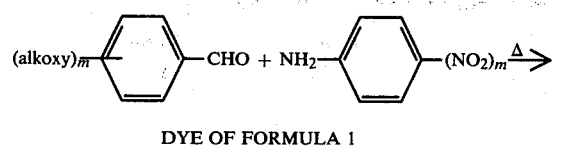

DYE OF FORMULA 1

As also disclosed in these Patents, the yellow ortho, ortho' dihydroxy azomethine dyes of Formula 1 can be chrome-complexed with a substantially colorless ligand to provide 1:1 chrome-complexed yellow dye developers. The particularly preferred 1:1 chrome complexed yellow dye developers are those of the following general formula:

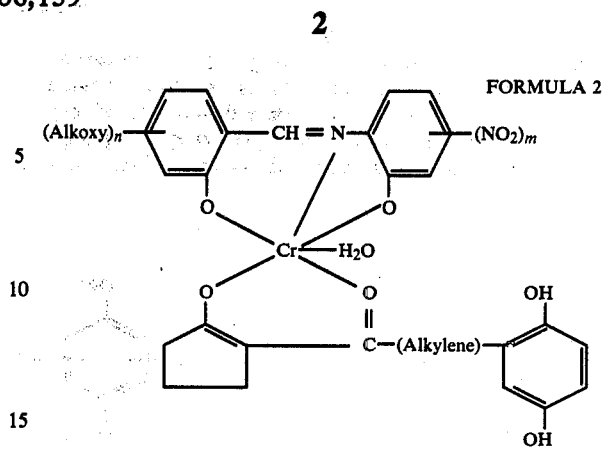

where, m and n are 1 or 2, (alkoxy) has from 1–8 carbon atoms and —alkylene— has from 1–6 carbon atoms.

1:1 chrome complexed yellow azomethine dyes of the above Formula 2 have excellent performance characteristics in terms of color as well as stability. In fact, a chrome complexed azomethine of Formula 2 which conforms to the following specific formula has enjoyed extensive success in commercial diffusion transfer, photographic film units.

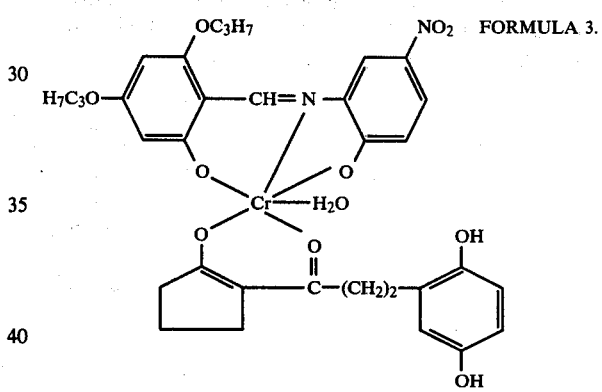

With each —OC$_3$H$_7$ being normal propanol.

This invention presents to the art novel benzaldehydes having a silver halide developing substituent. These novel benzaldehydes are valuable intermediates particularly useful in the preparation of yellow azomethine dyes having a silver halide developing capability and especially chrome complexed yellow azomethine dye developers having performance characteristics substantially equivalent to and in some respects, superior to yellow azomethine dye developers known to the art.

SUMMARY OF THE INVENTION

The novel benzaldehydes of the present invention are those of the following general formula:

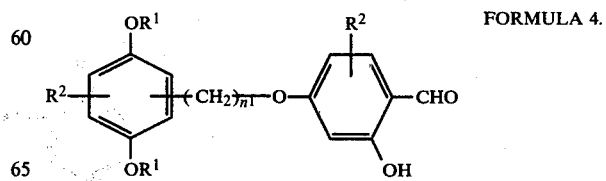

FORMULA 4.

Where: $n^1$ is the integer 1–8, each $OR^1$ is hydroxy or a protective group such as an acyloxy, benzyloxy, ethyloxy, alkoxy, acetoxy or like groups which can be converted or removed such as by hydrolysis to provide the dihydroxy phenyl silver halide developing moiety or substituent, the particularly preferred $R^1$ groups being carbomethoxy or carboethoxy and $R^2$ can be a substituent such as alkyl, alkoxy or halogen and benzaldehydes having such substituents are included within the scope of the claims.

The novel benzaldehydes of Formula 4 are valuable intermediates particularly useful in the preparation of yellow azomethine dyes having a silver halide developing capability. An illustrative preparation of such yellow dyes is as follows:

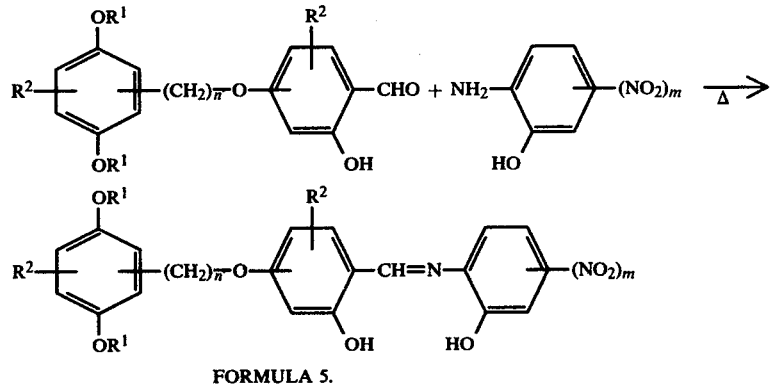

FORMULA 5.

Representative preferred yellow azomethine dyes of Formula 5 include the following:

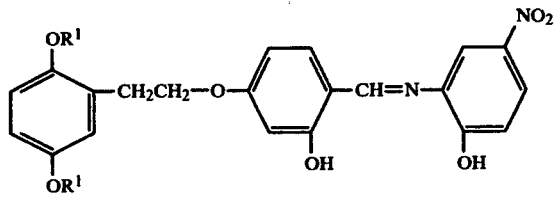

FORMULA 6

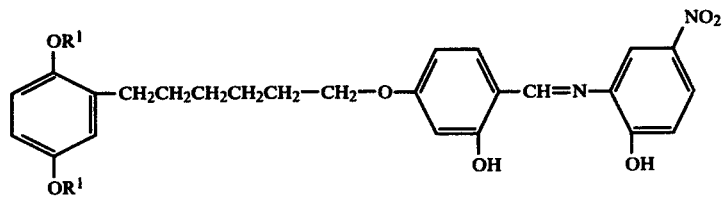

FORMULA 7

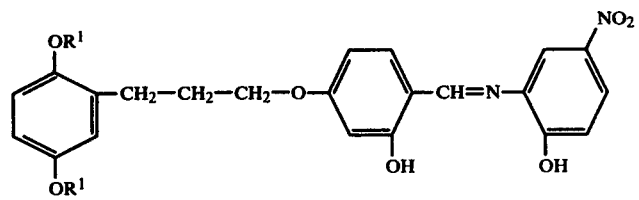

FORMULA 8

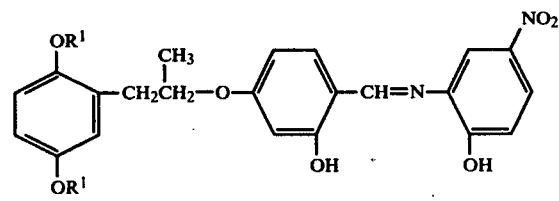

FORMULA 9

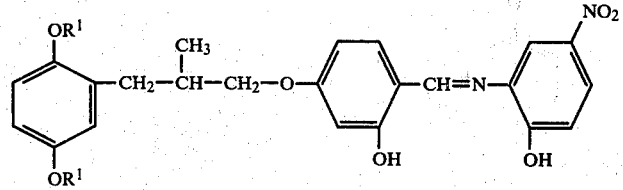

FORMULA 10

Where each $OR^1$ in the above formulae is —OH, —OCO$_2$CH$_3$, or —OCO$_2$C$_2$H$_5$.

As can be seen from Formulae 6–10, the yellow ortho, ortho' azomethine dyes produced from the novel benzaldehydes of the present invention are actually dye developers. That is, the dyes have a silver halide developing substituent as an integral part of the organic dye molecule. This feature of having a silver halide developing capability as an integral part of the dye provides distinct advantages particularly in the formation of metal complexes of the yellow dye developers with other complexable dyes or ligands and particularly with dyes or ligands also having silver halide developing substituents. For example—as will be illustrated later—a 2:1 chrome complexed yellow azomethine dye developer of Formula 11 shown below has especially desirable performance characteristics in photographic products and processes particularly in terms of color stability.

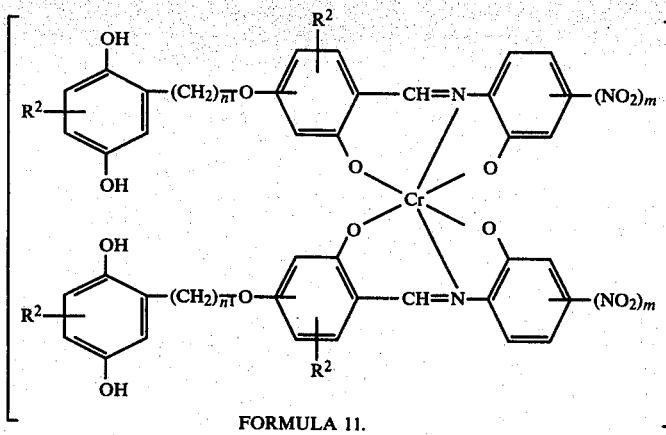

FORMULA 11.

Where: M is any cation that does not impair photographic processing of the dye developer and can be among others, H$_3$O, a metal ion, or a quaternary ammonium salt including onium salts as an integral part of the dye moiety and, $R^2$, $n^1$ and m are as defined before.

The invention, as well as details relating to the manners for making and using it, will be more fully appreciated by the following description of the preferred embodiments taken with FIGS. 1–5.

DESCRIPTION OF THE DRAWINGS

FIGS. 4 and 5 graphically depict dye stability data obtained in Examples 9 and 11 respectively.

DESCRIPTION OF THE PREFERRED EMBODIMENTS

Figure 1:
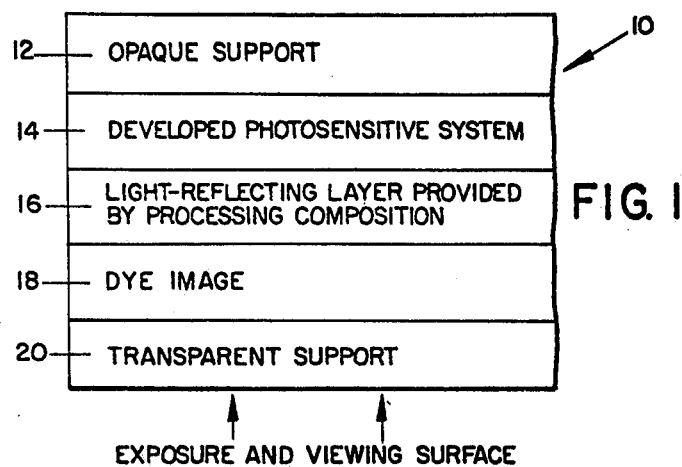
FIGS. 1–3 are simplified, schematic views of arrangements of essential elements of film units having dye developers prepared from the novel benzaldehydes of this invention. The film units are shown after exposure and processing.

The preferred preparation of the novel benzaldehydes of the present invention essentially involves two steps. The first step involves reacting a di-OR' substituted phenyl alcohol with a p-toluene sulfonyl chloride (tosyl chloride) and this first step can be illustrated by the following general reaction scheme:

STEP 1.

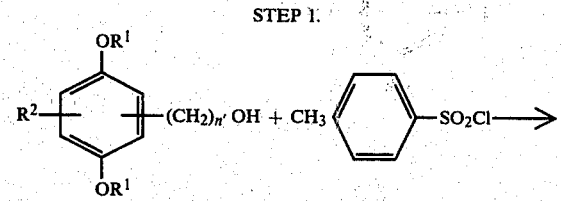

FORMULA 12          FORMULA 13

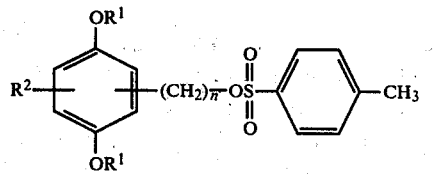

FORMULA 14

The second step involves the reaction of the tosylate product of step 1 (Formula 14) with a metal bis (resorcaldehyde) and this reaction can be illustrated by the following general reaction scheme:

STEP 2.

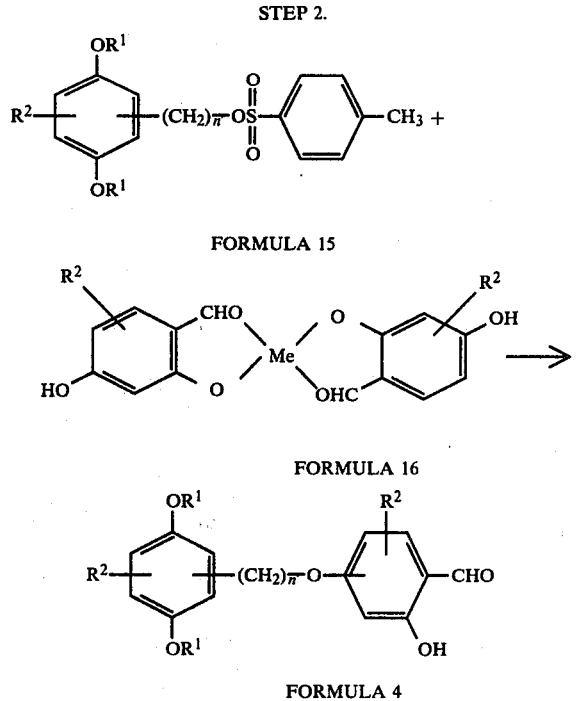

FORMULA 15

FORMULA 16

FORMULA 4

The metal bis (resorcaldehyde) of Step 2 (Formula 16) can be prepared by the reaction of a dihydroxybenzaldehyde with a metal (preferably copper) acetate monohydrate according to the following general reaction scheme:

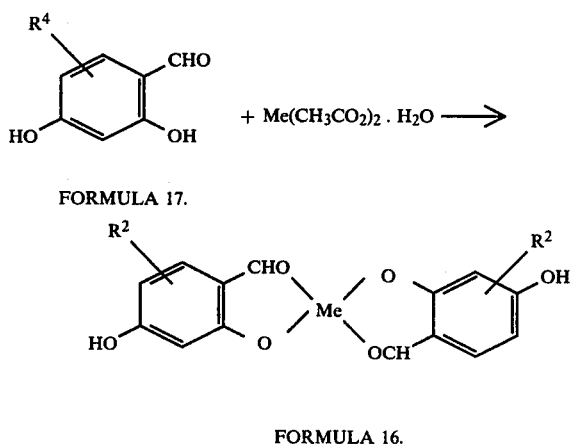

FORMULA 17.

FORMULA 16.

Details relating to the synthesis involved in the preparation of the novel benzaldehydes of this invention and to the preparation of 2:1 chrome complexes of the dye developers using the novel benzaldehydes will be better appreciated by reference to the following illustrative examples.

EXAMPLE 1

This example illustrates a preparation of an intermediate used in preparing a compound of Formula 12. The illustrative preparation involves the following reaction scheme:

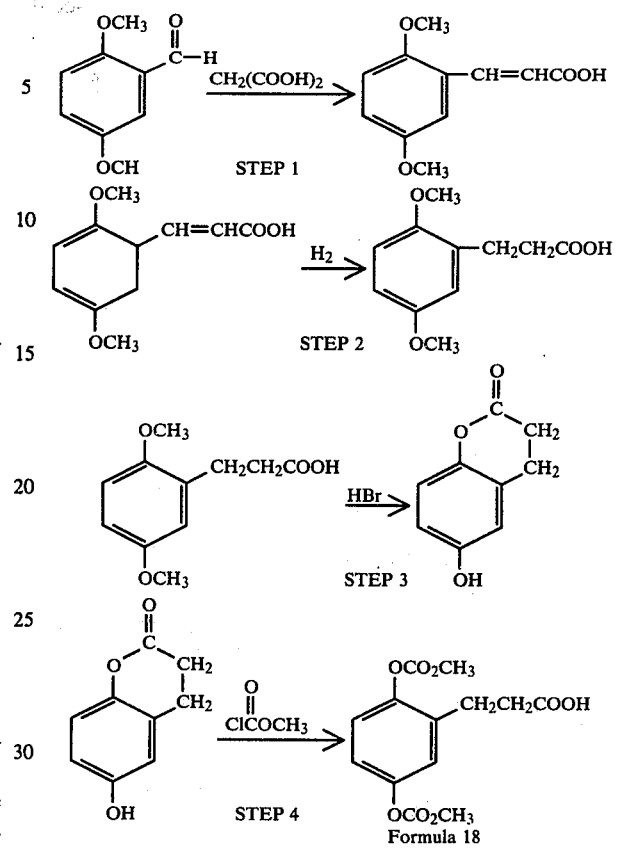

Step 1

The following ingredients were placed in a 5 liter 3 neck flask:

| 2,5-dimethoxybenzaldehyde | 447 grams |
|---|---|
| malonic acid | 559 grams |
| pyridine | 1080 grams |

The mixture was heated to 50° C. to obtain solution; then 40 mls. of piperdine were added and the reaction mixture heated at 80°–85° C. for 2 hours followed by refluxing for an additional 3 hours. The solution was cooled (overnight), poured into 11 liters of $H_2O$ and acidified slowly with 1 liter conc. HCl. to provide the product dimethoxy cinnamic acid which was filtered and washed with water.

Step 2

The following ingredients were placed in a 2 liter Parr bottle:

| dimethoxy cinnamic acid | 200 grams |
|---|---|
| isopropyl alcohol | 1100 mls. |
| Pd/BaSO$_4$ (5%) | 10 grams |

The hydrogenation of the dimethoxy cinnamic acid was carried out to theoretical uptake. The catalyst (Pd/BaSO$_4$) was filtered and the solution was treated with activated charcoal and then stripped to dryness to recover the dimethoxy hydrocinnamic acid.

Step 3

5.3 kgs. of 2,5-dimethoxyhydrocinnamic acid were dissolved in 5 liters 48% HBr solution. The reaction mixture was brought to reflux to distill off all the low boiling material up to 120° C. Refluxing was continued for about 3 hours. After cooling the mixture to room temperature, the precipitate was filtered off and washed well with water.

Step 4

A solution of 730 gms. NaOH in 12.5 liters H₂O was deaerated and kept under a blanket of nitrogen; then, 750 gms. of the lactone formed in Step 3 were added to it. The reaction mixture was stirred at room temperature for 2 hours and then cooled to 10° C. 2.0 kgms. methyl chloroformate were added at a slow enough rate to maintain the temperature at 10° C. The reaction mixture was stirred for an additional ½ hour and acidified to pH 2.0 with 1.8 liter 10% HCl solution. The water was decanted from the oil which formed, the oil was allowed to solidify slowly (overnight) to provide a crude yield of dicarbomethoxyphenyl propionic acid.

The crude yield of dicarbomethoxyphenyl propionic acid was purified by dissolving 200 gms. of the product of Step 4 in 2 liters of ligroin. The solution was heated to 80° C. and 1 liter benzene was added to dissolve the crude while the temperature was maintained at 80° C. The solution was treated with activated charcoal and filtered hot. On cooling, the pure product precipitated out. (Some oil formed at first but solidified on standing.) The product was then filtered and washed with hexane.

EXAMPLE 2

This example illustrates a preparation of a compound of Formula 12 and particularly relates to a preparation of a 3-(2', 5' dicarbomethoxyphenyl) propanol (Formula 19). The illustrative preparation involves the following reaction scheme:

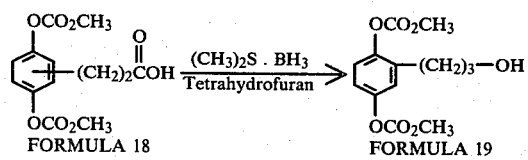

A nitrogen atmosphere was maintained by slowly flowing N₂ through a 2 liter, three neck flask while 68.08 gms dicarbomethoxyphenyl propionic acid (Formula 18) (0.2087 M) was added to 543 mls of anhydrous tetrahydrofuran. The dicarbomethoxyphenyl propionic acid dissolved readily and the solution was slowly stirred at 20°-25° C. While maintaining a slow flow of N₂ and maintaining the solution at a temperature of about 21° C., 18.40 gms (0.23 M) of borane methyl sulfide was added slowly over ½ hour with good stirring.

The slow flow of N₂ was continued while the mixture was stirred for 4½-5 hours at about 21° C. Then, 315 mls of methanol were added slowly with stirring to convert any excess borane to volatile borates.

The mixture was then filtered and volatiles were stripped off on a rotary evaporator using high vacuum and a hot water bath. The yield was 64.5 gms. of a clear yellow viscous liquid which eventually crystallized to a white solid soluble in CHCl₃ and methanol. The yield obtained was 98.7% of theoretical.

EXAMPLE 3

This example illustrates a preparation of a compound of Formula 15 and particularly relates to preparation of 3-(2', 5'-dicarbomethoxyphenyl) propyl-p-tosylate. The illustrated preparation involves the following reaction scheme.

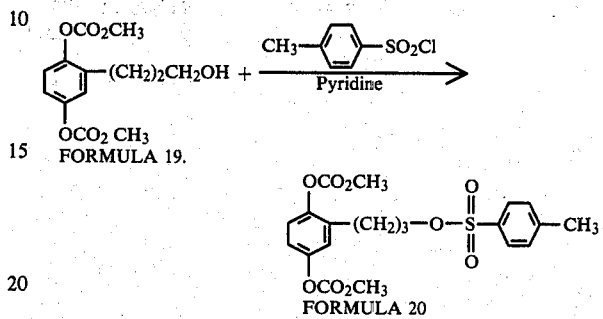

67.5 gms. of the dicarbomethoxyphenyl propionic alcohol (Formula 19) were dissolved at room temperature in 1220 mls. of pyridine in a 2 liter flask. The solution was then cooled to 0° C. While stirring the solution and maintaining the temperature at about 0° C., 82.5 gms. of p-toluenesulfonyl chloride were added as a solid, portion wise. After the addition, the mixture—tightly sealed to keep dry—was kept overnight in a refrigerator at 3° C.

The reaction mixture was then precipitated by adding the mixture to a well stirred cold dilute aqueous HCl solution (7,800 mls, ice cold distilled water plus1,520 mls conc. HCl.) and continuing the stirring for 1½ to 2 hours. The precipitate was oily at first but gradually became solid with stirring and trituration. The water was decanted, cold dilute HCl added again and stirring and trituration continued for another 1½ to 2 hours. A white solid was filtered off, washed with water and air dried overnight at room temperature. (The product should never be heated above room temperature.) Product yield was 100.7 gms. of white solid, m.p. 75°-76° C. and soluble in methylene chloride. The product should be stored at temperatures of 3° C. or lower.

| Properties of Compound: | MOL.WT.: 466.49 | MOL.FORMULA: SO₉C₂₂H₂₆ |
|---|---|---|
| m.p. | Color and State: | Solv.: |
| 75°-75.5° C. | White Solid | Methylene Chloride, CHCl₃ |

Elemental Analysis: Found: 56.86%C; 5.72%H; 6.71%S: Theory: 56.64%C, 5.62%H; 6.87%S.

EXAMPLE 4

This example illustrates a preparation of a compound of Formula 16 and particularly the preparation of cupric bis(resorcaldehyde). The illustrated preparation involved the following reaction scheme:

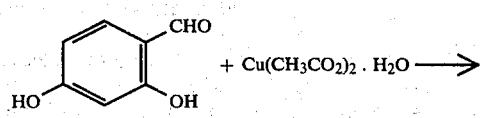

-continued

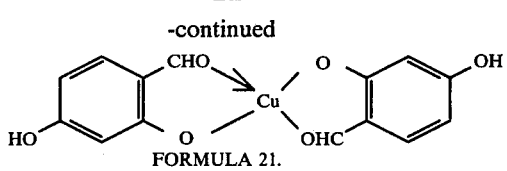
FORMULA 21.

19.97 gms (0.1 M) of cupric acetate monohydrate were dissolved in a room temperature solution of 50% aqueous methanol and the solution was gravity filtered to remove trace insolubles.

27.62 gms (0.2 M) of 2,4-dihydroxybenzaldehyde were dissolved in 50% aqueous methanol warmed slightly on a steam bath; the solution was then cooled to room temperature.

The 2,4-dihydroxybenzaldehyde solution was added to the well stirred solution of cupric acetate monohydrate and a green solid product precipitated almost immediately, but stirring was continued at room temperature for about one hour.

The product was filtered, washed several times with water; then several times with methanol and finally, several times with ether. The product was dried for one hour at 60° C. and 31.06 gms of a light green solid were obtained (91.96% theoretical yield).

EXAMPLE 5

This example illustrates a preparation of a compound of Formula 4 and particularly a preparation of a 2 hydroxy-4-[3'(2",5"-dicarbomethoxyphenyl)-n-propoxyl]-benzaldehyde. The illustrated preparation involves the following reaction scheme:

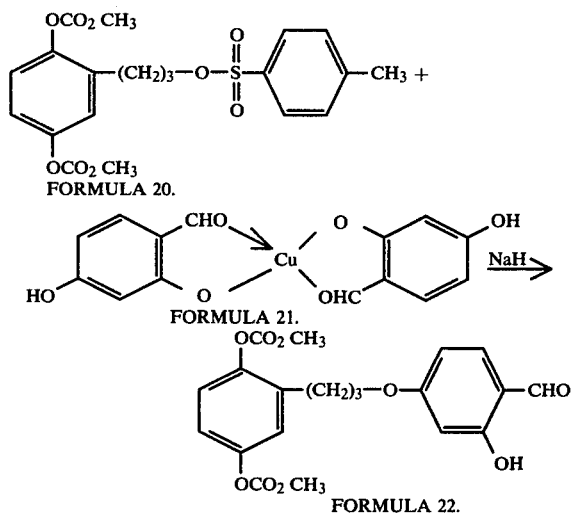

16.90 gms. of cupric bis(resorcaldehyde) (Formula 21) were dissolved in 170 mls. hexamethyl phosphoric triamide in a 1 liter flask having $N_2$ flow, 4.11 gms of a 57% NaH/oil mixture were added carefully with good stirring; there is a slight exotherm and some foaming due to $H_2$ evolution. Stirring was continued for 2½ hours at which time a dark green solution was obtained. 43.84 gms of 3-(dicarbomethoxyphenyl-P propyl-p-tosylate (Formula 20) dissolved in 180 mls. hexamethylphosphoric triamide were added to the green solution and the resulting solution was stirred overnight at room temperature and under a $N_2$ flow.

The product was precipitated in 10 volumes cold, dilute aqueous HCl solution and then extracted from the oily mixture by shaking it three times with ether. The final ether solution was shaken with aqueous $Na_2CO_3$ and then with water. The product was then dried with anhydrous $MgSO_4$. 33.40 gms of product was obtained as a viscous yellow-tan semi-solid. (82.60% of theoretical yield).

The dicarbomethoxy protective groups of the product of this Example can be removed by hydrolysis with mineral acids in manners known to the art to provide the compound of the following formula:

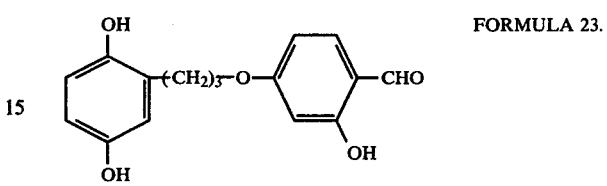
FORMULA 23.

However in the preferred preparations of yellow azomethine dyes of Formula 5 which follow, the protective groups are retained and removed later.

EXAMPLE 6

This example illustrates the preparation of a yellow azomethine dye of Formula 5 and particularly illustrates the preparation of a compound of the following formula:

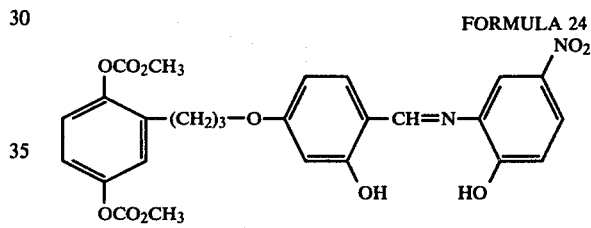
FORMULA 24

The illustrated preparation involves the following reaction scheme:

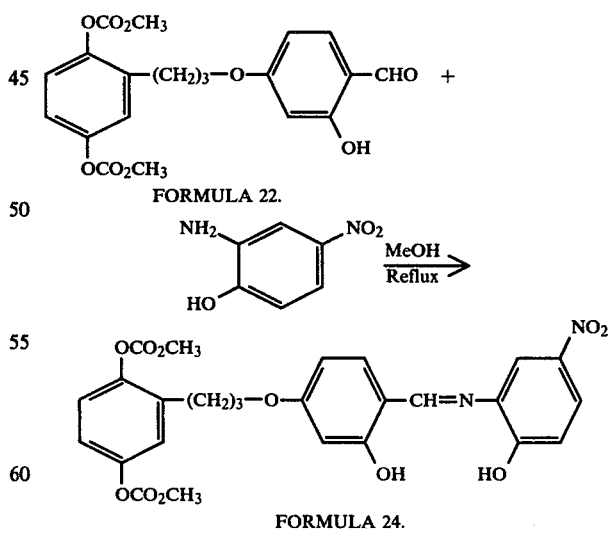
FORMULA 24.

In a 500 ml flask with a magnetic stirrer, reflux condenser and drying tube, 25.37 gms of 2 hydroxy-4-[3' (2",5] dicarbomethoxyphenyl)-n-propyl] benzaldehyde were dissolved in 102 mls refluxing methanol. 9.67 gms of 4-nitro-2-aminophenol dissolved in 39 mls of hot methanol were added to the benzaldehyde solution. In less than a minute, a very heavy yellow precipitate came out of solution. Stirring and refluxing were continued for 2 hours.

The mixture was cooled to about 0° C. and the yellow solid product filtered off and dried to constant weight giving 20.18 gms of yellow-orange product. (59.5% theoretical yield).

| Properties of Compound: | Color & State: | Soly.: |
|---|---|---|
| | Yellow-Orange solid | DMF;DMSO;Warm THF; Warm Dioxane. |
| UV.Visible: Solvent DMF | λ max 460 nm ε max 26,400 | |

EXAMPLE 7

This example illustrates a preparation of a 2:1 chrome complex of the product of Example 6. The illustrated preparation involves the following reaction scheme:

having a magnetic stirrer and reflux condenser with drying tube. The mixture was stirred and heated at 95° to 100° C. for 1¾ hours until a solution was obtained. The solution was then refluxed for 15 to 20 minutes.

The reaction solution was precipitated by stirring the solution in 2 liters of cold dilute aqueous HCl solution. The yellow solid product was filtered off and washed several times with distilled water. Yield of product was 18.78 gms of a tan solid (89.5% theoretical yield).

| Properties of Compound | Color & State: | Soly.: | Methyl Cellosolve, DMF, DMSO |
|---|---|---|---|
| | Tan-solid | | |
| UV,Visible: Solvent | λ max 445 nm ε max 41,500 | | |

EXAMPLE 8

This example illustrates a procedure for converting the dicarbomethoxy groups of the 2:1 chrome complex of Example 7 to dihydroxy groups to provide the 2:1 chrome complexed yellow azomethine dye developer

FORMULA 24.

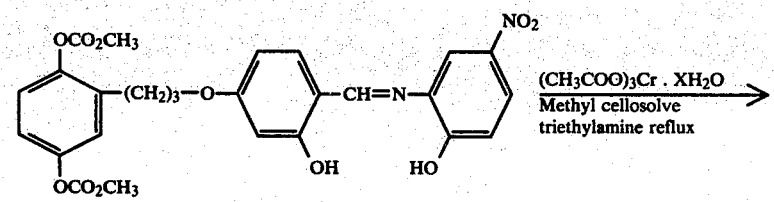

FORMULA 25.

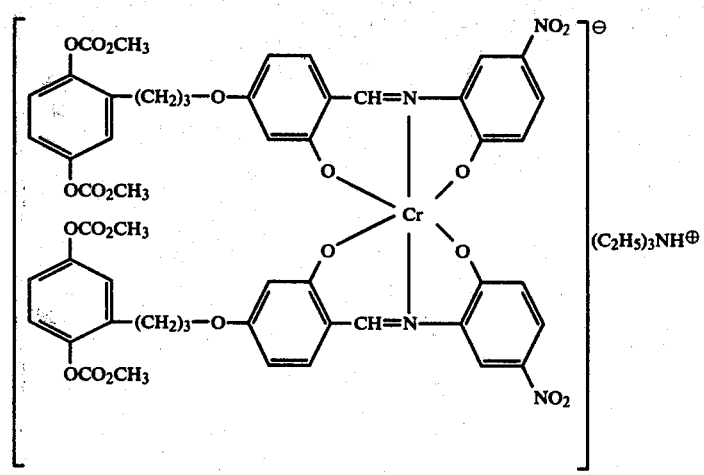

19.77 gms of the compound of Formula 24, 9.04 gms of (CH₃COO)₃Cr H₂O, 181 mls methyl cellosolve and 11.11 gms of triethylamine were added to a 3 neck flask of the following formula:

FORMULA 26.

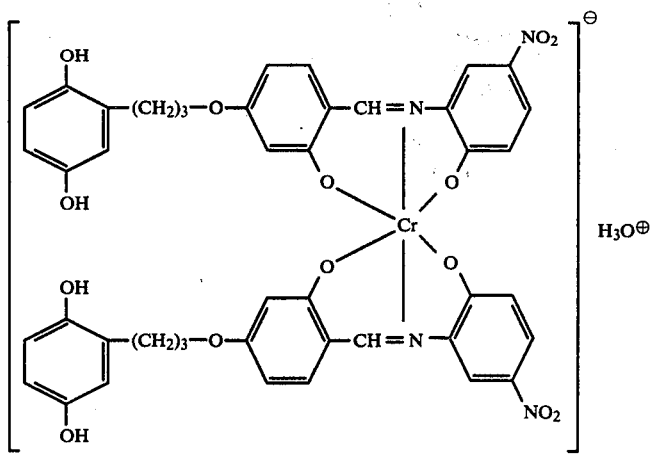

The illustrated procedure involves the following reaction scheme:

FORMULA 25.

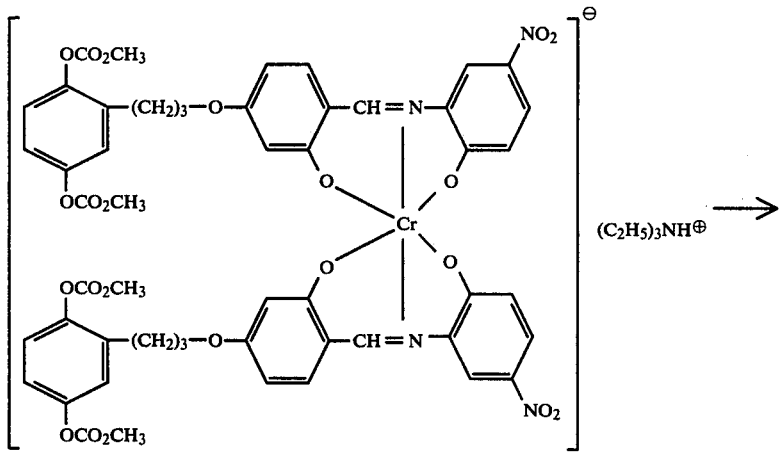

FORMULA 26.

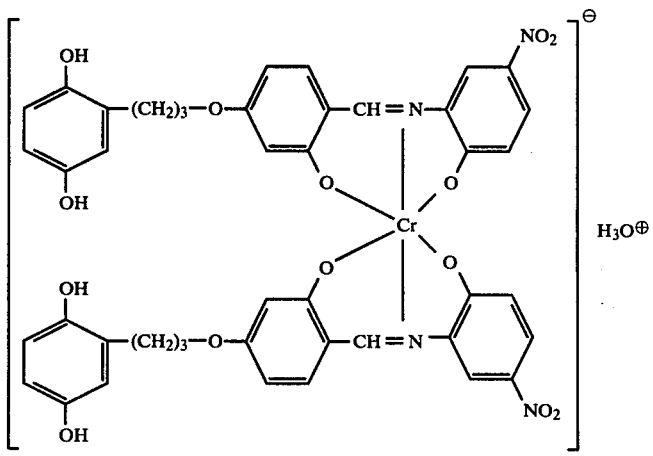

18.00 gms of the 2:1 chrome complexed dye of Formula 30 were dissolved in 200 mls methyl cellosolve at room temperature. $N_2$ bubbled into the solution to deaerate it. Then with $N_2$ slowly passing over the solution, 250 mls of a 5% (aqueous) NaOH solution, also deaerated, was gradually added with good stirring. There is a very mild exotherm. The solution was stirred under slow $N_2$ flow for 45 minutes plus 15 minutes while it was cooled down to about 5° C. 500 mls of cold 10% (aqueous) HCl solution (also deaerated) was added slowly to the well stirred cold reaction solution and the yellow tan solid product precipitated out. The product was filtered off, washed several times with distilled water and dried to constant weight. Product yield was 14.79 gms of tan solid.

Properties of Compound:
- MOL.WT.: 915.79
- MOL.FORMULA: $CrN_4O_{15}C_{44}H_{39}$
- Color & State: Tan Solid
- Soly.: Methyl Cellosolve; CMF; DMSO; dilute aqueous alkali
- UV,Visible: PANo. 20,362 $\lambda$ = 445 nm
- Solvent Methyl Cellosolve: $\epsilon$ = 38,000

Elemental Analysis: Product + 2H$_2$O of Hydration

| | | %C | %H | %N | %Cr | %ASH |
|---|---|---|---|---|---|---|
| Found: | | 55.68 | 4.54 | 5.73 | 5.51 | 10.45 |
| Theory: | | 55.52 | 4.55 | 5.89 | 5.46 | |

Yellow azomethine dye developers prepared from the novel benzaldehydes of this invention are particularly useful in diffusion transfer photographic products and processes. The chrome complexed azomethine dye developer of Example 8 has been found to be particularly advantageous when used in integral negative positive film units of the type discribed in detail in U.S. Pat. Nos. 3,415,644 and 3,647,437.

A representative film unit of this type is shown as 10 FIG. 1 and includes a light-reflecting layer provided by a light-reflecting pigment in a processing composition initially present in a rupturable processing container (not shown) and distributed after photosensitive layer(s) 14 is photoexposed through transparent support 20 and image-receiving layer 18. Processing compositions used in such film units are aqueous alkaline photographic processing compositions comprising an opacifying system which include a titanium dioxide pigment as the light-reflecting agent, preferably in combination with an optical filter agent described in detail in U.S. Pat. No. 3,647,437. When the processing composition is distributed over photoexposed portions of photosensitive system 14, a light-reflecting layer 16 comprising the titanium dioxide is provided between image-receiving layer 18 and photosensitive layer 14. Application of the processing composition initiates development of photoexposed photosensitive layer(s) 14 in manners well known to the art to establish an image-wise distribution of diffusible image-providing material which can comprise silver but preferably comprises one or more dye image-providing material. The diffusible image-providing material(s) is transferred through permeable, light-reflecting titanium dioxide-containing layer 16 where it is mordanted, precipitated or otherwise retained in known manner in image-receiving layer 18. The transfer image is viewed through transparent support 20 against light-reflecting layer 16.

Figure 2:
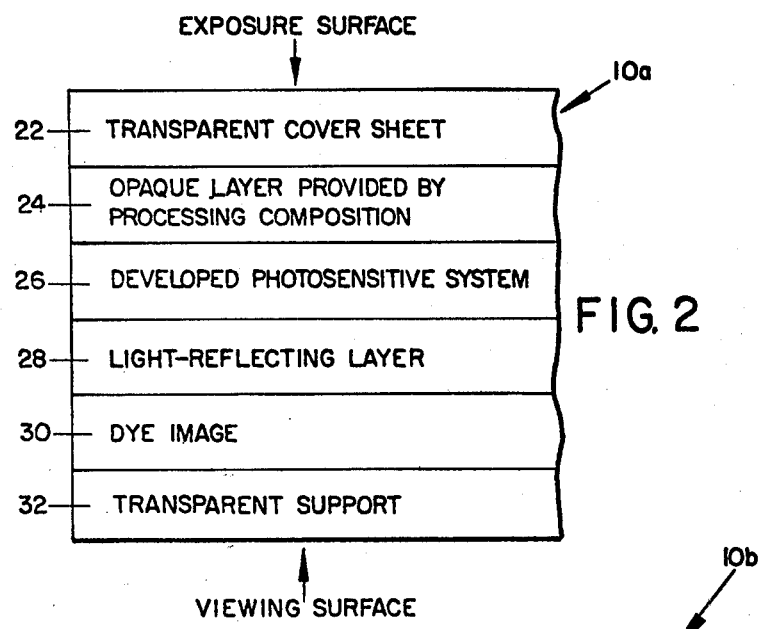

FIG. 2 shows an arrangement of essential elements of an integral negative-positive film unit of the type described in U.S. Pat. No. 3,594,165 and British Pat. No. 1,330,524 following exposure and processing. The film unit 10a includes a processing composition initially retained in a rupturable container (not shown) and distributed between cover sheet 22 and photosensitive system or layer 26 after photoexposure of photosensitive layer(s) 26 through transparent cover sheet 22. Processing compositions used in such film units are aqueous alkaline photographic processing compositions which include an opacifying system comprising an opaque pigment which need not be—and usually is not—light-reflecting. After distribution of the processing composition between transparent cover sheet 22 and photo-exposed photosensitive layer 26, an opaque layer 24 is installed which protects layer 26 from further photoexposure through cover sheet 22. Like the film units of FIG. 1, as an after opaque layer 24 is installed, and processing composition initiates developing of photoexposed photosensitive layer 26 to establish an image-wise distribution of the image-providing materials in manners well known to the art. For example, the processing composition alone may cause development or developing agents may be in the processing composition initially and/or the agents may be in the film unit so that they may be carried to layer 26 by the processing composition. The imagewise distribution is transferred through permeable titanium dioxide containing reflecting layer 28 to dye image layer 30 for viewing through transparent support 32 against the reflecting pigment containing layer 28. Oftentimes an opaque layer (not shown) is positioned between light reflecting layer 28 and photosensitive layer 26.

Figure 3:
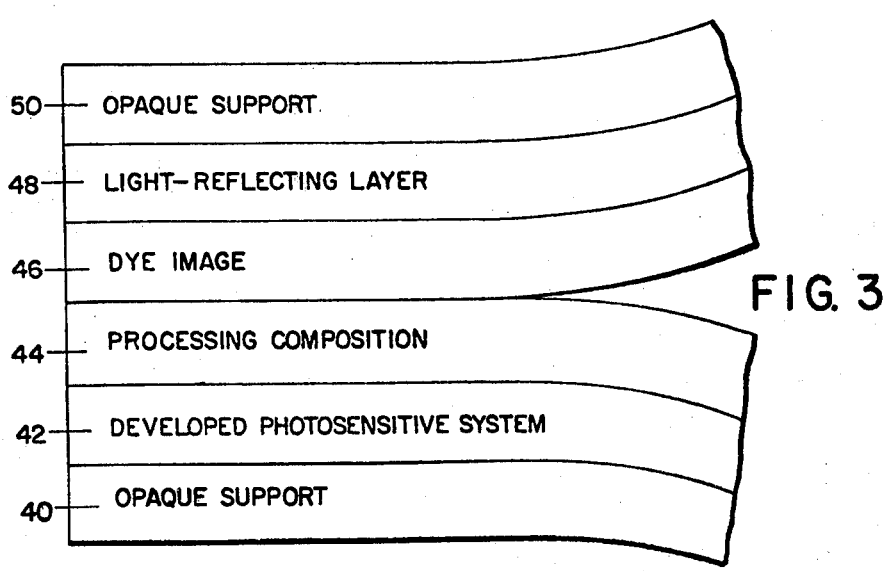

The novel yellow dye developers of the present invention also may be utilized in film units designed to be separated after processing, such as those described in U.S. Pat. No. 2,983,606. Such a diffusion transfer film unit of the present invention is shown in FIG. 3 as 10b. The film unit shown there comprises a photosensitive element having an opaque support 40 carrying a photosensitive system containing layer(s) 42. In film units of this type the photosensitive element is photoexposed and a processing composition 44 is then distributed over the photoexposed system. During processing an image-receiving element comprising dye image layer 46 carried by support 50—preferably opaque—is superposed on the photoexposed photosensitive element. Like the film units of FIGS. 1 and 2, the processing composition permeates layer(s) 42 to provide an imagewise distribution of diffusible dye image-providing materials which is transferred to dye image layer 46. Unlike the film units of FIGS. 1 and 2, however, the transferred dye image is viewed in layer 46 against light-reflecting background 48 after separation of the image-receiving element from the photosensitive element.

Example 9 which follows presents a comparison of the performance characteristics of the 2:1 chrome complexed yellow dye developer of Formula 26 and a 1:1 chrome complexed yellow dye developer extensively used in commercial film units (the 1:1 chrome complexed dye developer of Formula 3) The comparison involved diffusion transfer film units of the type shown in FIG. 1 and having a multicolor photo-sensitive elements which contained the following cyan and magenta dye developers:

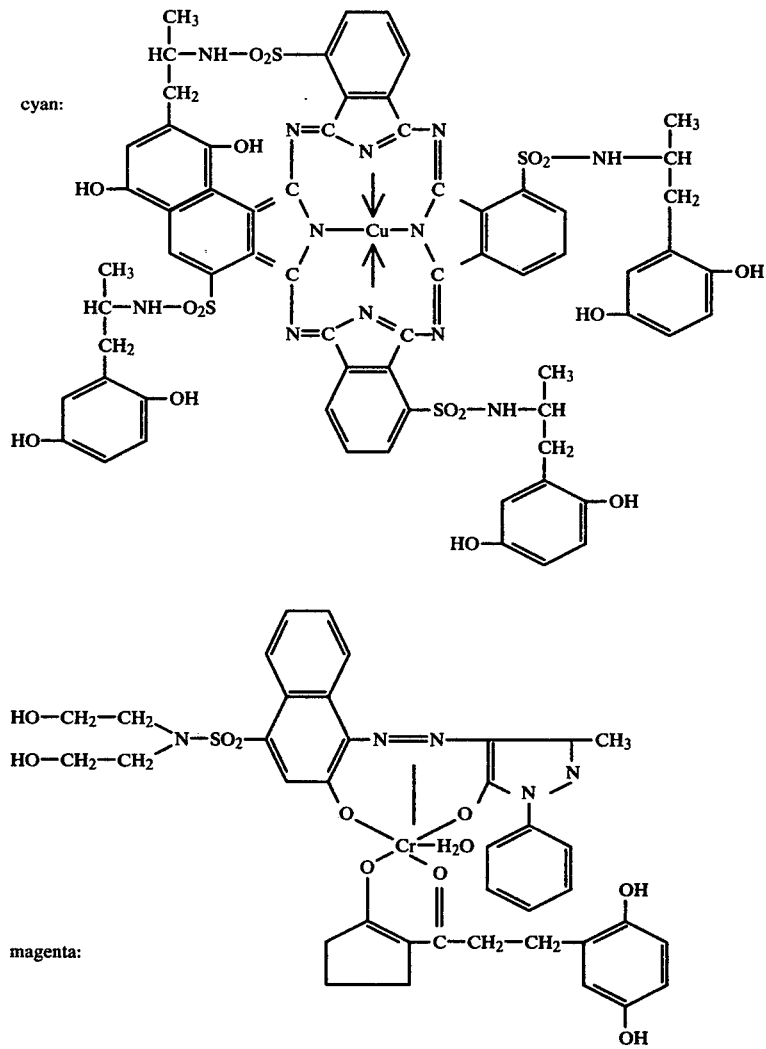

cyan:

magenta:

Also, except for variations in the yellow dye developer layer which are explained in Example 9, the photosensitive elements of the film units of Example 9 were prepared by coating a gelatin-subcoated, 4 mil, opaque polyethylene terephthalate film base with the following layers:

1. a layer of cyan dye developer and 2-phenylbenzimidazole (antifoggant) dispersed in gelatin and coated at a coverage of about 58 mgs./ft.$^2$ dye, about 22 mgss/ft.$^2$ of 2-phenyl benzimidazole and about 112 mgs./ft.$^2$ of gelatin;

2. a red-sensitive gelatino silver iodobromide emulsion coated at a coverage of about 80 mgs./ft.$^2$ of silver and about 104 mgs./ft.$_2$ of gelatin;

3. a layer of a 60-30-4-6- tetrapolymer of butylacraylate, diacetone acrylamide, styrene and methacrylic acid and polyacrylamide coated at a coverage of about 428 mgs./ft.$^2$ of the copolymer and about 23 mgs./ft.$^2$ of polyacrylamide;

4. a layer of magenta dye developer and 2-phenyl benzimidazole dispersed in gelatin and coated at a coverage of about 60 mgs./ft.$^2$ of dye, about 21 mgs./ft.$^2$ of 2-phenyl benzimidazole and about 40 mgs./ft.$^2$ of gelatin;

5. a green-sensitive gelatino silver iodobromide emulsion coated at a coverage of about 30 mgs./ft.$^2$ of silver and about 43 mgs./ft.$^2$ of gelatin;

6. a layer containing the tetrapolymer referred to above in layer 3 and polyacrylamide coated at a coverage of about 230 mgs./ft.$^2$ of copolymer and about 20 mgs./ft.$^2$ of polyacrylamide;

7. a layer of a yellow dye developer and 2-phenyl benzimidazole dispersed in gelatin and coated at the coverage specified in Example 9.

8. a blue-sensitive gelatino silver iodobromide e emulsion layer coated at a coverage of about 110 mgs./ft.$^2$ of silver and about 52 mgs./ft.$^2$ of gelatin and 9. a layer of carbon black dispersed in gelatin coated at a coverage to provide about 4 mgs./ft.$^2$ of carbon black and about 40 mgs./ft.$^2$ of gelatin.

The image-receiving elements of the film units of Example 9 were prepared by coating a transparent 4 mil polyethylene terephthalate film base with the following layers:

1. as a polymeric acid layer, the partial butyl ester of polyethylene/maleic anhydride copolymer at a coverage of about 2,500 mgs./ft.$^2$;

2. a timing layer containing about 40:1 ratio of a 60-30-4-6 tetra copolymer of butylacrylate, diacetone acrylamide, styrene and methacrylic acid and polyvinyl alcohol at a coverage of about 500 mgs./ft.$^2$; and 3. a polymeric image-receiving layer containing a 2:1 mixture, by weight, of polyvinyl alcohol and poly-4-vinylpyridine, at a coverage of about 300 mgs./ft.$^2$.

The so prepared image-receiving and photosensitive elements can be taped together with opaque tape extending around the edges to provide an integral film unit. A rupturable container retaining an aqueous alkaline processing solution was mounted in a fixed position on the leading edge of each of the elements, by pressure-sensitive tapes, so that, pressure applied to the container would rupture the container's marginal seal and its contents could be distributed between the image-receiving layer and the gelatin overcoat layer of the photosensitive element.

In each of the film units of Example 9, the aqueous alkaline processing composition comprised:

| | |
|---|---|
| Water | 1918 cc |
| Potassium hydroxide (85%) | 509 g. |
| N-phenethyl-α-picolinium bromide (50% solution in water) | 110.4 g. |
| Carboxymethyl cellulose (Hercules Type 7H4F providing a viscosity of 3,000 cps. at 1% in water at 25° C.) 95% solids | 80.3 g. |
| Titanium dioxide | 1842 g. |
| 6-methyl uracil | 9.3 g. |
| bis-(β-aminoethyl)-sulfide | 1.4 g. |
| Lithium nitrate | 4.8 g. |
| Benzotriazole | 34.6 g. |
| Colloidal silica aqueous dispersion (30% SiO$_2$) | 77.6 g. |
| N-2-hydroxyethyl-N,N',N'-tris carboxymethyl-ethylene diamine | 36.4 g. |
| Polyethylene glycol (molecular weight 6,000) | 22.7 g. |
| 4-amino pyrazolo pyrimidene | 11.3 g. |
| | 93.4 g. |
| | 20.8 g. |

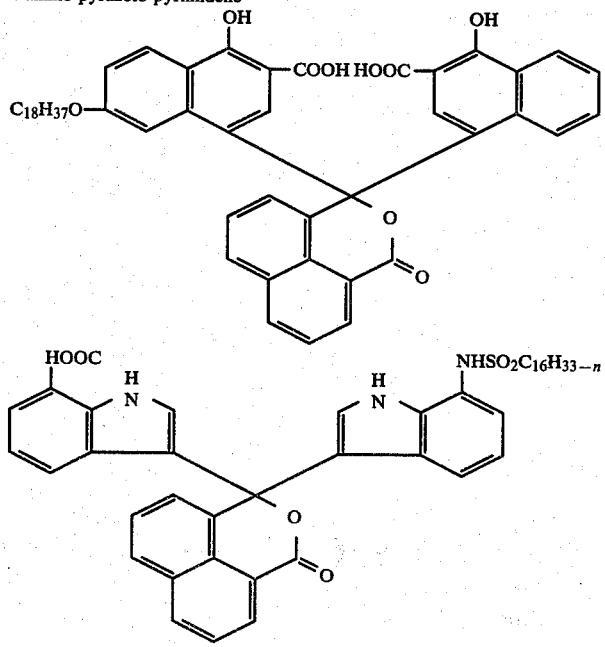

The photosensitive element of such prepared integral film units may be exposed through the transparent support of the image-receiving element, and a layer of the processing composition may be distributed by passing the film unit between a pair of pressure-applying rolls.

EXAMPLE 9

Figure 4:
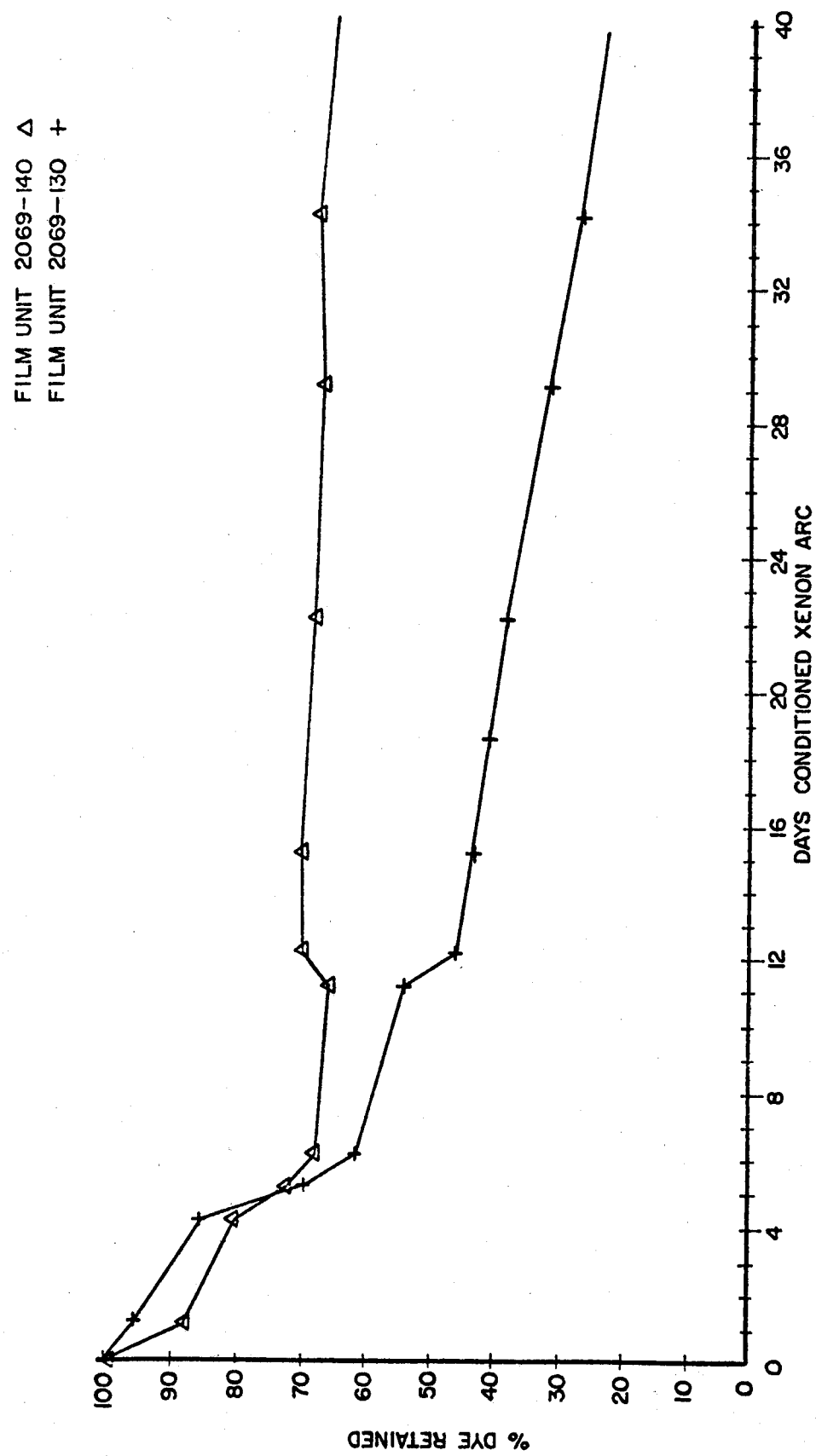

This example presents a comparison of dye stability measurements for two film units, one containing a 1:1 chrome complexed yellow dye developer of the prior art and the other containing a 2:1 chrome complexed yellow dye developer of this invention. FIG. 4 graphically depicts the dye stability measurements. The two film units had multicolor photosensitive elements prepared as described before and were substantially identical except for the yellow dye developer layers. In the film unit designated as 2069-140 of FIG. 4, the yellow dye containing layer contained the 2:1 chrome complexed yellow dye developer of Formula 26 and 2-phenyl benzimidazole dispersed in gelatin at a coverage of about 46 mgs./ft.$^2$ yellow dye developer, about 19.6 mgs./ft.$^2$ of 2-phenyl benzimidazole and about 18.1 mgs. gelatin. The film unit designated as 2069-130 of FIG. 4 had a yellow dye developer containing layer which contained the 1:1 chrome complexed yellow dye developer of Formula 3, 2-phenyl benzimidazole and gelatin at a coverage of about 67 mgs./ft.$^2$ yellow dye developer, about 18 mgs./ft.$^2$ phenyl benzimidazole and about 33 mgs./ft.$^2$ gelatin. It will be noted that the coverages of yellow dye developers in each film unit are different (46 mgs./ft.$^2$ v. 67 mgs./ft.$^2$). This difference, however, was intended and is based on considerations involving such factors as the extinction coefficient, the molecular weight and the molecular structure of each dye developer to estimate coverages for each dye developer which can provide approximately equivalent yellow optical densities for each exposed and processed film unit.

The film units were exposed to two meter candle seconds through a yellow filter and processed by passing each film unit between a pair of pressure-applying rolls to thereby distribute a layer of processing composition about 0.0028" thick between the image-receiving layer and the gelatin/carbon black overcoat of the photosensitive element. Under such exposure conditions only yellow dye was transferred to the image-receiving layer and both processed film units had comparable yellow colored images.

The processed film units were maintained at room temperature for twenty-four hours and then the dye stability of each unit was determined by exposing each unit to the condition of a Xenon Arc Weatherometer over a period of 40 days and periodically measuring the percent yellow dye retained for each unit. During this forty day period, the light output for the Weatherometer ranged between 7000 to 9000 foot candles. FIG. 4 graphically depicts the data obtained over the forty day period and the data shows improved stability performance characteristics for the 2:1 chrome complexed yellow dye developer of this invention.

EXAMPLE 10

This example illustrates a preparation of a 1:1 chrome complex azomethine yellow dye developer of the present invention. The illustrated preparation involves the following reaction schemes:

Step 1.

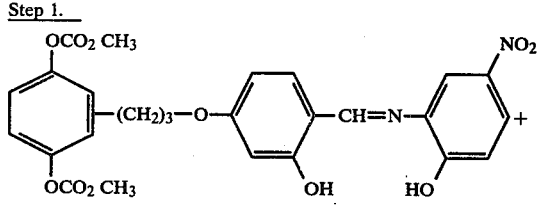

$$Cr Cl_3 \cdot 6H_2O \longrightarrow$$

FORMULA 24.

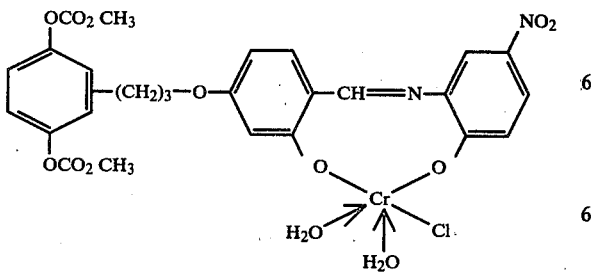

FORMULA 27.
Step 2.

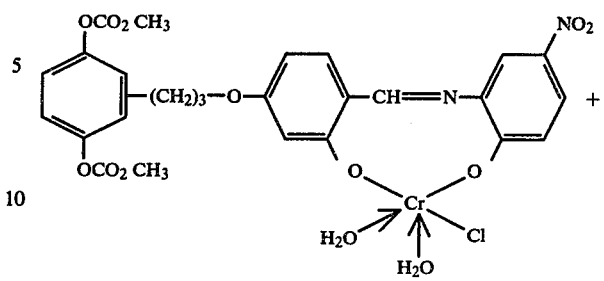

FORMULA 27.

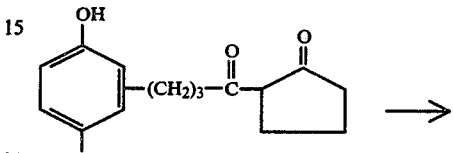

FORMULA 28.

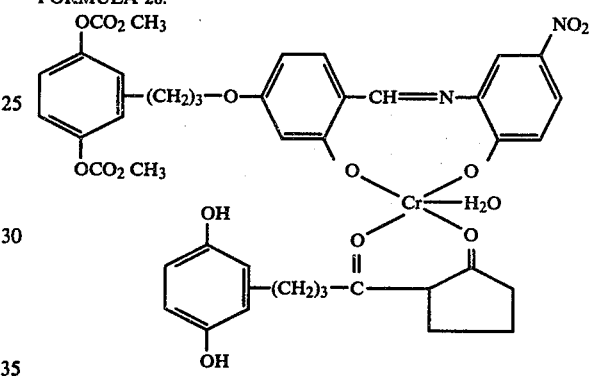

FORMULA 29.
Step 3.

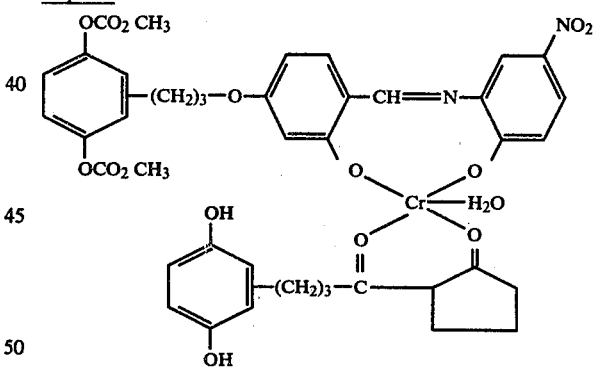

$$\xrightarrow[HCl]{NaOH}$$

FORMULA 29.

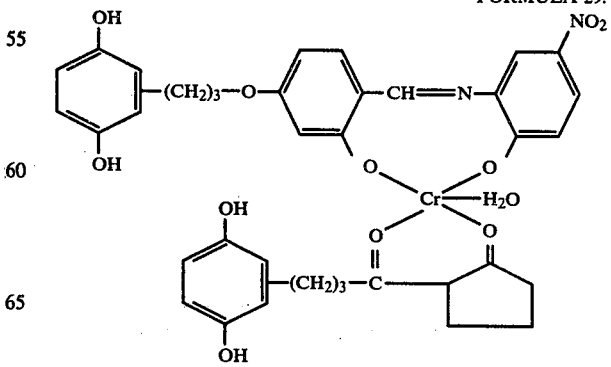

FORMULA 30.

Step 1

The following ingredients were added to a 2-liter, 3-neck, round bottom flask having a vertical reflux condenser and a $N_3$ inlet and outlet:

| | |
|---|---|
| Cr Cl$_3$ . 6H$_2$O | 25.03 gms. |
| Dimethyl formamide (anhydrous) | 409 mls. |
| Benzene (anhydrous) | 588 mls. |

The solution was refluxed with stirring to azeotrope out water with benzene (13.8 mls. $H_2O$ collected) and then all benzene was distilled off.

26.7 gms. of the compound of Formula 24 were added to the anhydrous Cr Cl$_3$/dimethyl formamide solution, and the mixture was refluxed for 45 minutes.

The reaction solution was cooled and precipitated into 6,700 mls. distilled water and stirred for about 20 minutes. The precipitate was filtered and washed twice on the funnel with room-temperature, distilled water. After air-drying overnight, the precipitate was placed in an oven heated to 67° C. for 15 minutes and then placed in a vacuum oven heated to 52° C.; a high vacuum was pulled for about 2½ hours. Yield of product (Formula 27) was 20.71 gms. of a yellow-tan powder (69.12% theoretical).

Step 2

A round-bottom, 250 ml. flask having a magnetic stirrer, a vertical reflux condenser and a $N_2$ inlet and outlet was flushed with dry $N_2$ while heated at 75° to 80° C. The following ingredients were then added:

| | |
|---|---|
| Compound of Formula 27 | 7.00 gms. |
| Compound of Formula 28 (98% pure) | 2.80 gms. |
| IR-45 Amberlite Ion Exchange Resin | 0.58 gms. |
| Methyl cellosolve | 90 mls. |

The reaction mixture was stirred at 75°–80° C. for a total of 10 hours. The ion exchange resin (insoluble) was filtered off, and the solution was sealed under $N_2$ overnight at room temperature. The product was precipitated by adding the solution (slowly) to 1,800 mls. distilled water at room temperature with good stirring. A fine yellow precipitate was filtered off, stirred well in 500 mls. distilled water and filtered again. The product was placed in a vacuum oven heated to 55° C. (with drierite present) and a high vacuum was pulled on the oven for about 3½ hours. Yield of product (Formula 29) was 8.58 gms. of yellow powder (88.50 theoretical).

Step 3

The following ingredients were added to a 1-liter, 3-neck, round-bottom flask having a magnetic stirrer, $N_2$ inlet and outlet and dropping funnel:

| | |
|---|---|
| Compound of formula 29 | 8.30 gms. |
| Methyl cellosolve | 80 mls. |

$N_2$ was bubbled through the solution to deaerate it, and the system was flushed with $N_2$. A solution containing 15.02 gms. Na OH in 142 mls. $H_2O$ was placed in the dropping funnel and deaerated. While stirring the solution in the flask and with an $N_2$ flow through the flask, the Na OH solution was added slowly (a slight exotherm was noted). The contents of the flask were stirred at room temperature for about 55 minutes.

The flask was then cooled in an ice bath; and, while stirring and with an $N_2$ flow, a cold dearated solution of 31.05 mls. concentrated HCl in 280 mls. $H_2O$ was added (slowly). The product precipitated out as a tan solid which was filtered off and air-dried.

After drying, the product—now a tan-yellow solid—was stirred in 150 mls. distilled water, filtered and placed in a vacuum oven (drierite was present) for 5 hours. The vacuum oven was heated to a temperature of 48°–50° C., and a high vacuum was pulled on the oven. Yield of yellow powder (Formula 30) was 6.87 gms. (98.91% theoretical).

| Properties of Compound: | Color & State: | Soly.: |
|---|---|---|
| | Yellow-tan Solid powder | Methanol, DMF Methyl cellosolve |
| U.V. Visible: | | |
| Solvent | max 443 | |
| Methyl cellosolve | max 18,400 | |

EXAMPLE 11

This example presents a comparison of the light stability characteristics of the 1:1 chrome complexed yellow dye developer of Example 10 and the 1:1 chrome complexed yellow dye developer of Formula 3. This comparison involved diffusion transfer monochrome film units which had substantially the same image receiving elements, the same processing compositions and the same photosensitive elements—except for the yellow dye developer used. The film unit designated as 22-092 in FIG. 5 had a yellow dye developer layer comprising the dye developer of Example 10 dispersed in gelatin and coated at a coverage of about 40 mgms/ft$^2$ dye developer and about 210 mgms/ft$^2$ gelatin.

The film units were exposed to two meter candle seconds through a yellow filter and processed by passing each film between pressure-applying members to distribute a layer of processing composition about 0.0022" thick between the image-receiving element and the photosensitive element. Both processed film units had comparable yellow color. Dye stability measurements were made as described in Example 9 except that each film unit was dried for three days at 120° F. before being placed in the arc. FIG. 5 graphically depicts the data obtained over a forty-seven day period and the data indicates that the dye developer of Example 10 had substantially better stability performance characteristics than the dye developer of Formula 3.

From the above description, it should be apparent that the present invention presents to the art novel benzaldehydes particularly useful in preparing yellow dye developers having a desirable degree of performance characteristics in terms of color as well as stability. Accordingly, many modifications can be made in details of the above examples offered for the purposes of illustrating preferred embodiments of the invention without departing from the spirit and scope of the invention defined in the claims.

What is claimed is:

1. A process for the synthesis of benzaldehydes comprising reacting a compound represented by the formula

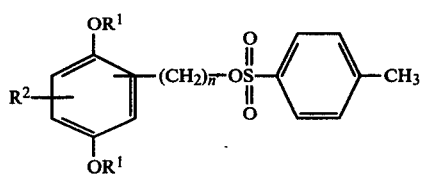

with a compound represented by the formula

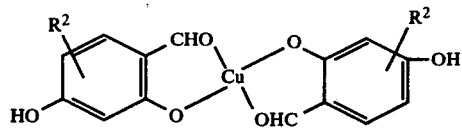

to form a compound represented by the formula

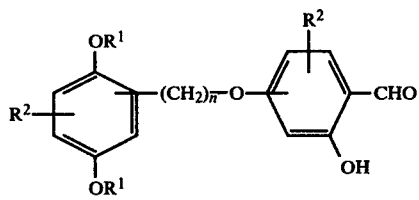

wherein each $OR^1$ group is hydroxy or a protective group which can be converted or removed to provide a dihydroxyphenyl moiety, $R^2$ may be alkyl, alkoxy or halogen, and $n'$ is an integer from 1 to 8.

2. A process as defined in claim 1 wherein $R^1$ is hydrogen, carbomethoxy or carboethoxy.

3. A process as defined in claim 1 wherein the compound formed is represented by the formula

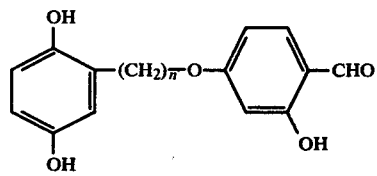

4. A process as defined in claim 1 wherein the compound formed is represented by the formula

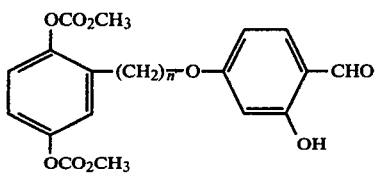

5. A process as defined in claim 1 wherein the compound formed is represented by the formula

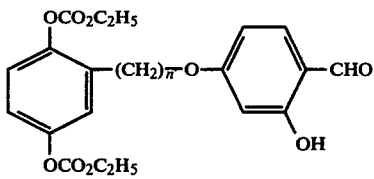

6. A process as defined in claim 1 wherein the compound formed is represented by the formula

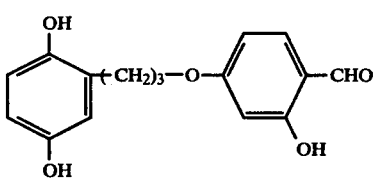

7. A process as defined in claim 1 wherein the compound formed is represented by the formula

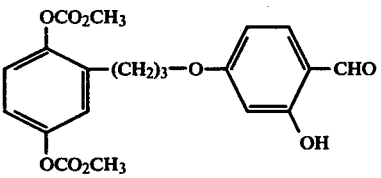

8. A process as defined in claim 1 wherein the compound formed is represented by the formula:

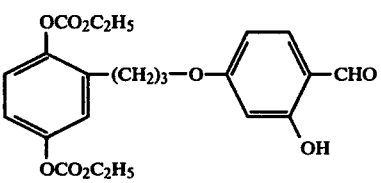

* * * * *